(12) United States Patent
Felt et al.

(10) Patent No.: US 8,123,713 B2
(45) Date of Patent: Feb. 28, 2012

(54) SYSTEM AND METHOD FOR COLLECTING PLASMA PROTEIN FRACTIONS FROM SEPARATED BLOOD COMPONENTS

(75) Inventors: Thomas J. Felt, Boulder, CO (US); Frank Corbin, III, Littleton, CO (US); Steven Gage Urdahl, Golden, CO (US)

(73) Assignee: Caridian BCT, Inc., Lakewood, CO (US)

( * ) Notice: Subject to any disclaimer, the term of this patent is extended or adjusted under 35 U.S.C. 154(b) by 388 days.

(21) Appl. No.: 12/429,266

(22) Filed: Apr. 24, 2009

(65) Prior Publication Data

US 2010/0042037 A1   Feb. 18, 2010

Related U.S. Application Data

(60) Provisional application No. 61/088,154, filed on Aug. 12, 2008, provisional application No. 61/093,892, filed on Sep. 3, 2008, provisional application No. 61/097,598, filed on Sep. 17, 2008, provisional application No. 61/120,763, filed on Dec. 8, 2008.

(51) Int. Cl.
*A61M 37/00* (2006.01)
*C02F 1/44* (2006.01)

(52) U.S. Cl. ............ 604/6.04; 604/6.01; 604/6.09; 604/6.11; 604/6.15; 210/781; 210/782; 210/645

(58) Field of Classification Search ............. 604/4.01, 604/5.01, 6.01, 6.02, 6.04, 6.09, 6.11, 6.15; 210/645, 781, 782

See application file for complete search history.

(56) References Cited

U.S. PATENT DOCUMENTS

| | | | |
|---|---|---|---|
| 4,276,140 A | 6/1981 | Jain | |
| 4,350,156 A | 9/1982 | Malchesky et al. | |
| 4,350,594 A | 9/1982 | Kawai et al. | |
| 4,351,710 A | 9/1982 | Jain | |
| 4,609,461 A | 9/1986 | Takata et al. | |
| 4,619,639 A | 10/1986 | Nosé et al. | |
| 4,687,580 A | 8/1987 | Malbrancq et al. | |
| 4,713,176 A | 12/1987 | Schoendorfer et al. | |
| 4,721,564 A | 1/1988 | Harada et al. | |
| 4,728,430 A * | 3/1988 | DiLeo et al. | 210/639 |
| 4,746,436 A | 5/1988 | Kopp et al. | |
| 4,776,964 A | 10/1988 | Schoendorfer et al. | |
| 4,780,205 A | 10/1988 | Murakami et al. | |
| 4,789,482 A | 12/1988 | DiLeo et al. | |
| 4,806,247 A | 2/1989 | Schoendorfer et al. | |

(Continued)

FOREIGN PATENT DOCUMENTS

EP 0264931 4/1988

(Continued)

OTHER PUBLICATIONS

International Search Report for PCT/US2009/048134, mailed Jan. 20, 2010.

(Continued)

*Primary Examiner* — Leslie Deak
(74) *Attorney, Agent, or Firm* — Edna M O'Connor; John R. Merkling; Laura B Arciniegas

(57) ABSTRACT

Method and apparatus for separating plasma from blood in a separation vessel and further separator the separated plasma into desired plasma proteins in a plasma separator fluidly connected to the separation vessel to receive the separated plasma.

33 Claims, 5 Drawing Sheets

U.S. PATENT DOCUMENTS

| | | | |
|---|---|---|---|
| 4,871,462 A | 10/1989 | Fischel et al. | |
| 4,911,833 A | 3/1990 | Schoendorfer et al. | |
| 4,985,153 A | 1/1991 | Kuroda et al. | |
| 5,008,012 A | 4/1991 | Hagihara et al. | |
| 5,141,490 A | 8/1992 | Fujii et al. | |
| 5,217,618 A | 6/1993 | Murakoshi | |
| 5,358,482 A | 10/1994 | Panzani | |
| 5,460,715 A * | 10/1995 | Kawamura et al. | 210/97 |
| 5,516,431 A | 5/1996 | Kawamura et al. | |
| 5,871,649 A | 2/1999 | Ofsthun et al. | |
| 5,954,971 A | 9/1999 | Pages et al. | |
| 6,669,905 B1 | 12/2003 | Mathias et al. | |
| 7,025,881 B2 | 4/2006 | Heim | |
| 7,267,771 B2 | 9/2007 | Gorsuch et al. | |
| 7,470,245 B2 | 12/2008 | Tu et al. | |
| 7,481,936 B2 | 1/2009 | Gorsuch et al. | |
| 7,563,376 B2 | 7/2009 | Oishi | |
| 2002/0033370 A1 | 3/2002 | Bainbridge et al. | |
| 2002/0062100 A1 * | 5/2002 | Pierce et al. | 604/6.01 |
| 2002/0099174 A1 | 7/2002 | Johnston et al. | |
| 2004/0182787 A1 | 9/2004 | Chevallet et al. | |
| 2006/0129082 A1 | 6/2006 | Rozga | |
| 2006/0186044 A1 | 8/2006 | Nalesso | |
| 2006/0226090 A1 | 10/2006 | Robinson et al. | |
| 2006/0287628 A1 * | 12/2006 | Hirabuki | 604/6.01 |
| 2007/0034579 A1 | 2/2007 | Dorian et al. | |
| 2008/0135502 A1 | 6/2008 | Pyo et al. | |

FOREIGN PATENT DOCUMENTS

| | | |
|---|---|---|
| KR | 2008/0052036 | 6/2008 |
| WO | WO01/58496 | 8/2001 |

OTHER PUBLICATIONS

International Search Report for PCT/US2009/048087, mailed Feb. 3, 2010.

* cited by examiner

SYSTEM AND METHOD FOR COLLECTING PLASMA PROTEIN FRACTIONS FROM SEPARATED BLOOD COMPONENTS

CROSS REFERENCE TO RELATED APPLICATIONS

This application claims benefit under 35 U.S.C. 119(e) of U.S. Provisional Application Nos. 61/088,154 filed Aug. 12, 2008; 61/093,892, filed Sep. 3, 2008, 61/097,598, filed Sep. 17, 2008 and 61/120,763, filed Dec. 8, 2008.

This application is related to U.S. Ser. No. 12/429,325 filed on Apr. 24, 2009.

BACKGROUND

For transfusions of blood and blood components, whole blood from a single donor is typically separated into three components: plasma, red blood cells and platelets. Each component may be used to treat a multiplicity of specific conditions and disease states. For example, the red blood cell component may be used to treat anemia and replace red blood cell loss due to bleeding, the concentrated platelet component may be used to control bleeding, and the plasma component may be given to patients to increase blood volume, or may be separated off-line after collection into individual plasma proteins such as fibrinogen, von Willebrand factor, Factor VIII, Factor IX, Anti-thrombin III, Fibrin sealant, thrombin, Alpha I and IVIG. Plasma from multiple donors may also be collected and combined or pooled together, and the combined plasma pool fractionated into the desired plasma proteins.

The separation of the collected plasma component into various protein or plasma components or fractions is called plasma fractionation. Such fractionation is typically done by large scale fractionators which combine plasma from many donors and concentrate individual plasma proteins by using the known techniques of cold alcohol fractionation (also known as Cohn fractionation) and chromatography.

There are traditionally two ways to obtain separated blood components from single donors. One way is to collect whole blood from donors and separate it into components at some time period after the whole blood collection. Using this method, whole blood is collected into approved containers that are pyrogen-free and sterile, and contain sufficient anticoagulant for the quantity of blood to be collected. Whole blood which is collected in this way is separated into components in a lab by a technician, and separation typically occurs from between about 2 and 8 hours after collection in the United States, and between about 2 to 24 hours in Europe.

Another way to separate whole blood into components is by using an apheresis device. These apheresis devices separate whole blood from a single donor, connected on-line to the device, into components automatically, and return any uncollected and unneeded blood components back to the donor during the collection procedure.

Apheresis devices may be used to separate the plasma component from the cellular components of a blood donation. Apheresis devices permit more frequent donations by a single donor due to the return of uncollected components.

BRIEF SUMMARY OF THE INVENTION

The invention may include a method of collecting plasma fractions comprising rotating a separation vessel, separating plasma from other blood components in the rotating separation vessel, providing separated plasma from the rotating separation vessel to a plasma separator, separating the plasma into plasma proteins using the plasma separator and collecting at least a portion of the plasma proteins.

A further aspect of the invention is an apheresis plasma separation system comprising a rotor, a separation vessel mounted on the rotor for rotating therewith wherein blood is separated into plasma and other components in the separation vessel during rotation of the rotor, a plasma separator fluidly connected to the separation vessel to receive the separated plasma from the rotating separation vessel, a membrane comprising hollow fibers in the plasma separator wherein the membrane can separate at least some plasma proteins from the separated plasma, and a collection container fluidly connected to the plasma separator for collecting the separated plasma proteins from the plasma separator.

Another aspect of the invention includes a method of predicting the concentration of proteins to be collected using a plasma separator comprising, determining the volume of fluid entering a plasma separator for a period of time, determining the volume of plasma proteins separated from plasma in the plasma separator and exiting the plasma separator for such period of time, predicting the concentration of plasma proteins exiting the plasma separator by determining the ratio of the inlet volume over the exit volume.

A further aspect of the invention relates to a plasma protein product produced by a method comprising separating plasma from other blood components in a rotating separation vessel, separating the plasma from the rotating separation vessel into plasma proteins, and further optionally concentrating the desired plasma proteins in a plasma fractionation process.

An additional aspect of the invention relates to a pre-connected disposable set including a removal/return assembly, a separation vessel fluidly connected to the removal/return assembly, a plasma collect assembly fluidly connected to the separation vessel including a membrane plasma separator, and a collection container fluidly connected to the membrane plasma separator.

DETAILED DESCRIPTION

It should be noted that like elements are represented using like numerals. This invention is described with reference to the TRIMA® automated collection system (manufactured and sold by CaridianBCT, Inc., Lakewood, Colo., USA) but it should be noted that any apheresis system, such as, but not limited to the COBE® SPECTRA system, SPECTRA OPTIA® system and the TRIMA ACCEL® automatic collection system also manufactured and sold by CaridianBCT, Inc. may be used without departing from the spirit and scope of the invention.

The invention also may be used with the apheresis systems of other manufacturers such as the Autopheresis C system manufactured by Fenwal, Inc. Lake Zurich, Ill., U.S.A. or the PCS system as manufactured by Haemonetics Corp. of Bainbridge, Mass.

Figure 1:
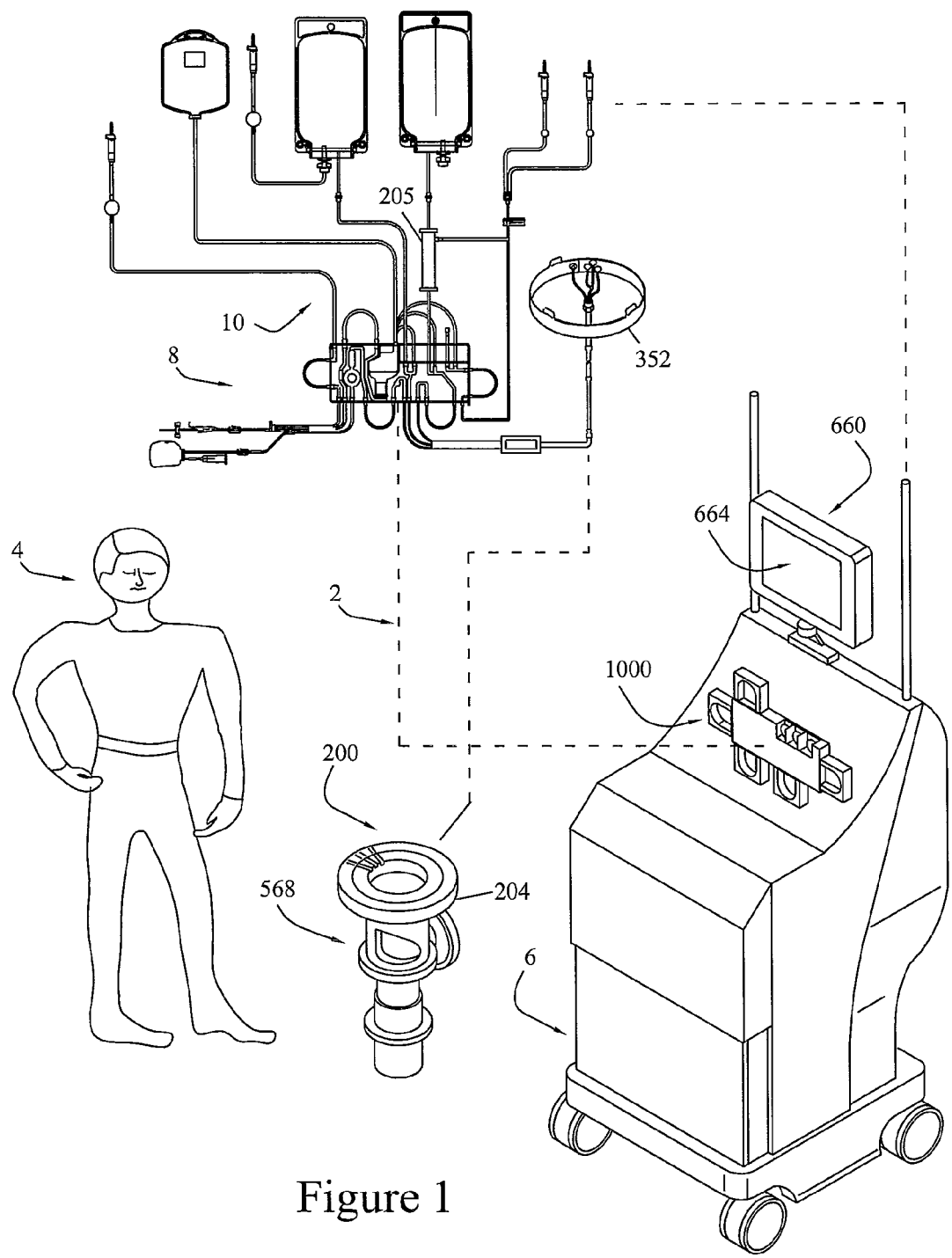
FIG. 1 is a schematic view of an apheresis system.

A blood apheresis system 2 is illustrated in FIG. 1 and allows for a continuous blood component separation process. Generally, in a continuous system, whole blood is withdrawn from a donor/patient 4 and provided to a blood component separation device 6 where the blood is separated into the individual blood components with at least one of these blood components being removed from the device 6 with the other components being returned to the donor. The continuous system 2 also provides for further separation or concentration of plasma into plasma proteins for collection.

In the blood apheresis system 2, blood is withdrawn from the donor/patient 4 and directed through a pre-connected disposable set 8 which includes an extracorporeal tubing circuit 10, a blood processing vessel 352 and a plasma separator or concentrator 205 which defines a completely closed and sterile system. The disposable set 8 is mounted on the blood component separation device 6 which includes a pump/valve/sensor assembly 1000 for interfacing with the extracorporeal tubing circuit 10, and a channel assembly 200 for interfacing with the disposable blood processing vessel 352.

The channel assembly 200 includes a channel housing 204 which is rotatably interconnected with a rotatable centrifuge rotor assembly 568 which provides the centrifugal forces required to separate blood into its various blood component types by centrifugation. The blood processing vessel 352 is inter-fitted into the channel housing 204 to fit with a groove or channel in the channel housing. Blood thus flows from the donor/patient 4, through the extracorporeal tubing circuit 10, and into the rotating blood processing vessel 352. The blood within the blood processing vessel 352 is separated into various blood component types and at least one of these blood component types (e.g., plasma, red blood cells) is continually removed from the blood processing vessel 352. The plasma component may then be further concentrated or separated into plasma proteins. Blood components which are not being retained for collection or for use in therapeutic treatments are also removed from the blood processing vessel 352 and returned to the donor/patient 4 via the extracorporeal tubing circuit 10. The blood processing vessel 352 may optionally be used for a platelet collection although such collection will not be described.

Operation of the blood component separation device 6 is controlled by one or more processors, not shown. In order to assist the operator of the apheresis system 2 with various aspects of its operation, the blood component separation device 6 includes a graphical interface 660 with a touch screen input/output device 664.

The apheresis system below will be described with respect to a red blood cell collection and a plasma protein collection. It is understood, however, that a plasma collection only may also occur if desired. If plasma collection only is desired, with subsequent separation and collection of plasma proteins, the system described below can be simplified. For example, the red blood cell collection assembly 950 could be deleted. Also the vent bag tubing subassembly 100 and the replacement fluid assembly 960 can be optional. Collecting plasma proteins only with no red blood cell collection can provide a simplified closed system.

Figure 2:
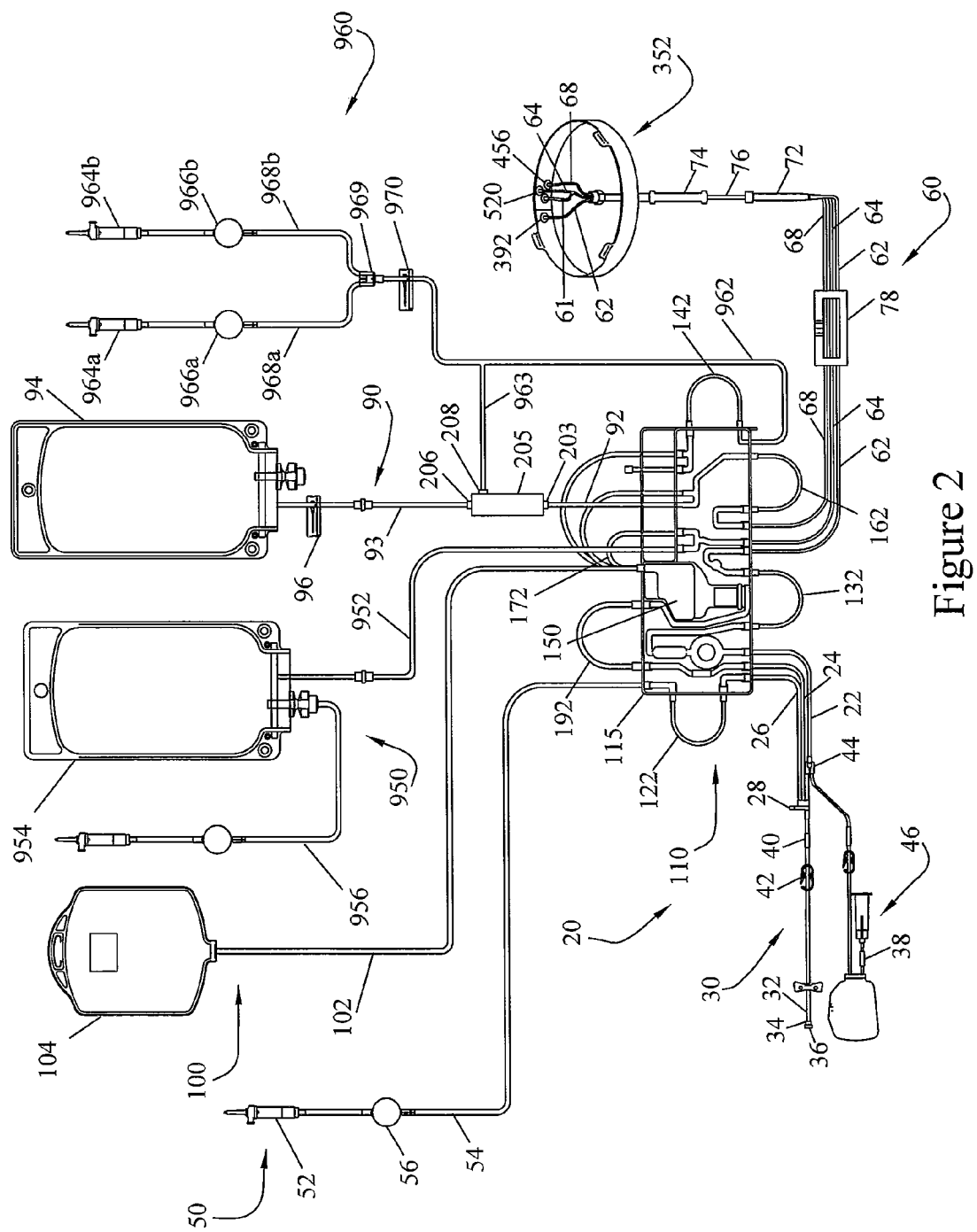
FIG. 2 is a schematic view of the blood separator/plasma separation tubing set for the system of FIG. 1.

As illustrated in FIG. 2, blood-primable pre-connected extracorporeal tubing circuit 10 comprises a cassette assembly 110 and a number of tubing assemblies 20, 50, 60, 950, 90, 100 and optionally 960 interconnected therewith. Generally, blood removal/return tubing assembly 20 provides a single needle interface between a donor/patient 4 and cassette assembly 110, and blood inlet/blood component tubing subassembly 60 provides the interface between cassette assembly 110 and blood processing vessel 352. An anticoagulant tubing assembly 50, plasma or plasma protein collection tubing assembly 90, red blood cell collection assembly 950 and vent bag tubing subassembly 100 are also interconnected with cassette assembly 110. A platelet collection tubing assembly could be included if it was further desired to collect platelets. Optionally, a replacement fluid sub-assembly 960 may be included. The extracorporeal tubing circuit 10 including the assemblies or sub-assemblies above and blood processing vessel 352 are interconnected to yield a closed disposable system or pre-connected disposable for a single use.

The blood removal/return tubing assembly 20 includes a needle subassembly 30 interconnected with blood removal tubing 22, blood return tubing 24 and anticoagulant tubing 26 via a common manifold 28. The needle subassembly 30 includes a needle 32 having a protective needle sleeve 34 and needle cap 36, and interconnect tubing 38 between needle 32 and manifold 28. Needle subassembly 30 further includes a D sleeve 40 and tubing clamp 42 positioned about the interconnect tubing 38. Blood removal tubing 22 may be provided with a Y-connector 44 interconnected with a blood sampling subassembly 46.

The blood removal/return assembly includes first integral passageway 190a connected to the bottom of reservoir 150, tubing loop 192 and second integral fluid passageway interconnected with tubing loop 192 and blood return tubing 24.

Cassette assembly 110 includes front and back molded plastic plates (not shown) that are hot-welded together to define a rectangular cassette member 115 having integral fluid passageways. The cassette assembly 110 further includes a number of outwardly extending tubing loops, described below, interconnecting various integral passageways. The integral passageways are also interconnected to the various tubing assemblies.

Figure 3:
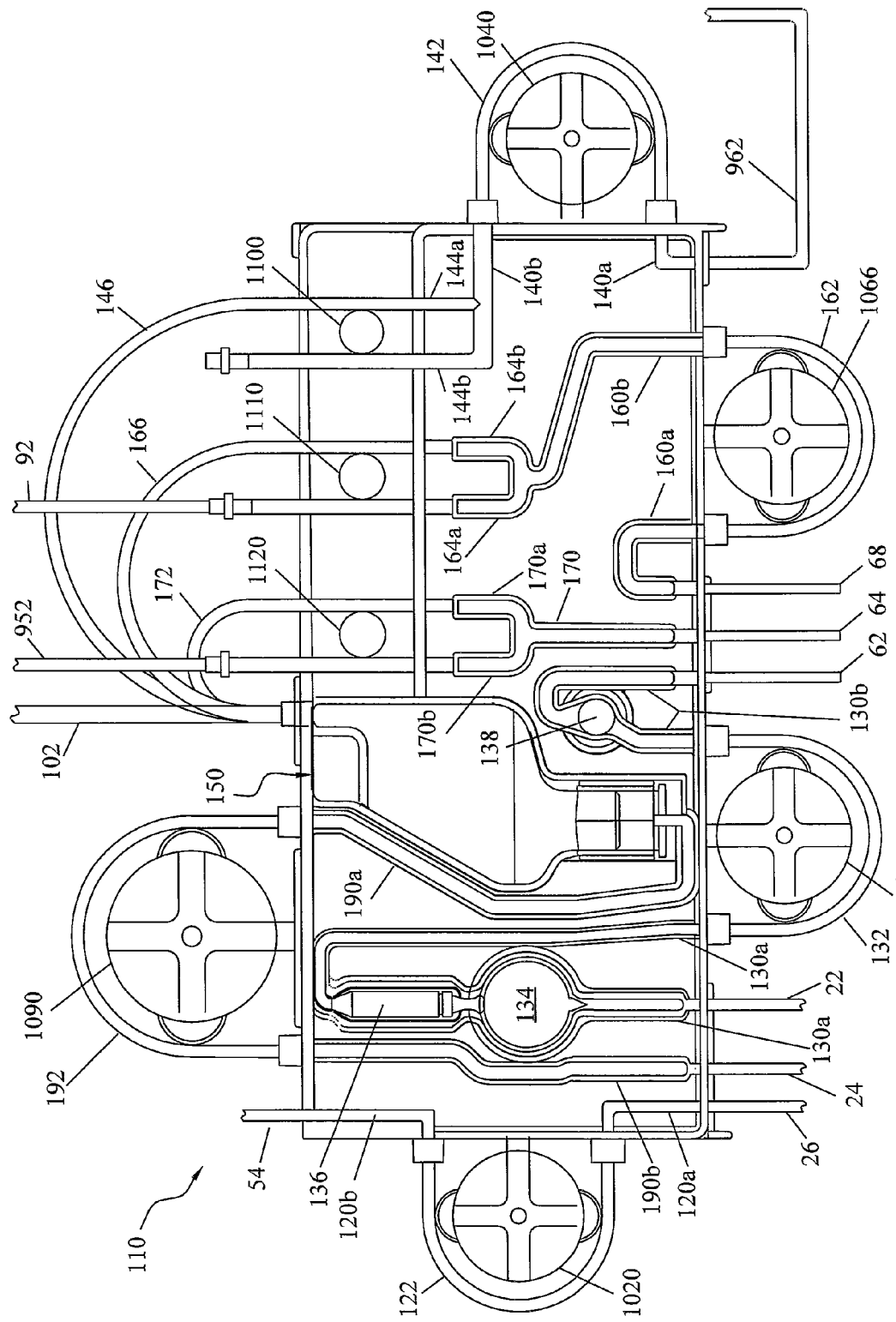
FIG. 3 is a schematic view of a detail of the tubing set of FIG. 2.

As seen in FIG. 3, cassette assembly 110 includes a first integral anticoagulant passageway 120a interconnected with the anticoagulant tubing 26 of the blood removal/return tubing assembly 20. The cassette assembly 110 further includes a second integral anticoagulant passageway 120b and a pump-engaging, anticoagulant tubing loop 122 between the first and second integral anticoagulant passageways 120a, 120b. The second integral anticoagulant passageway 120b is interconnected with anticoagulant tubing assembly 50. The anticoagulant tubing assembly 50 includes a spike drip chamber 52, (FIG. 2) connectable to an anticoagulant source, anticoagulant feed tubing 54 and a sterile barrier filter 56. During use, the anticoagulant tubing assembly 50 supplies anticoagulant to the blood removed from a donor/patient 4 to reduce or prevent any clotting in the extracorporeal tubing circuit 10.

Cassette assembly 110 also includes a first integral blood inlet passageway 130a interconnected with blood removal tubing 22 of the blood removal/return tubing assembly 20. The cassette assembly 110 further includes a second integral blood inlet passageway 130b and a pump-engaging, blood inlet tubing loop 132 between the first and second integral blood inlet passageways 130a, 130b. The first integral blood inlet passageway 130a includes a first pressure-sensing module 134 and inlet filter 136, and the second integral blood inlet passageway 130b includes a second pressure-sensing module 138. The second integral blood inlet passageway 130b is interconnected with blood inlet tubing 62 of the blood inlet/blood component tubing assembly 60.

Blood inlet tubing 62 is also interconnected with input port 392 of blood processing vessel 352 to provide whole blood thereto for processing. To return separated blood components to cassette assembly 110, the blood inlet/blood component tubing assembly 60 further includes a red blood cell (RBC) outlet tubing 64 with outlet port 520 and plasma outlet tubing 68 with outlet port 456. A control port for controlling the interface is shown at 61.

The blood inlet tubing 62, RBC outlet tubing 64, and plasma outlet tubing 68 all pass through first and second strain relief members 72 and 74 and a braided bearing member 76 there between. This advantageously allows for a sealess interconnection, as taught in U.S. Pat. No. 4,425,112. As shown, multi-lumen connectors 78 can be employed in the various tubing lines.

An optional replacement fluid tubing assembly 960 may be provided for delivery of replacement fluid such as sterile saline solution(s) (or replacement/exchange RBCs or plasma, e.g.) to the donor/patient 4. As shown, the replacement fluid assembly 960 includes at least a replacement fluid inlet tubing line 962 attached to the cassette 110 in fluid communication with an internal replacement fluid passageway 140a which is in turn connected to a replacement fluid tubing loop 142 which is connected back to the cassette 110 and an internal replacement fluid passageway 140b. Two further internal passageways or spurs 144a and 144b and a tubing loop 146 are also shown. Internal passageway 144b is blocked off to disallow any fluid flow therein or therethrough. No outlet tubing line is preferably connected thereto and passageway 144b may also be omitted.

The replacement fluid assembly 960 further preferably includes one or more spike assemblies 964a-964b with optional associated sterile barrier devices 966a-966b and tubing connection lines 968a-968b which may be connected to tubing line 962 via a Y-connector 969 as shown. One or more slide clamp(s) 970 may also be included. As the plasma proteins may be frozen before use the sterile barrier devices 966a-966b are optional.

Although the replacement fluid assembly is shown as introducing such fluid through 140a and tubing loop 142 such is only exemplary. In other words the fluid could be introduced through other tubing loops for return such as tubing loop 162 or such fluid could even be aspirated through tubing into the system.

The plasma outlet tubing 68 of blood inlet/blood component tubing assembly 60 interconnects with a first integral plasma passageway 160a of cassette assembly 110. Cassette assembly 110 further includes a pump-engaging, plasma tubing loop 162 interconnecting the first integral plasma passageway 160a and a second integral plasma passageway 160b. The second integral plasma passageway 160b includes first and second spurs 164a and 164b. The first spur 164a is interconnected to the plasma collection tubing assembly 90. The plasma collection tubing assembly 90 may be employed to collect plasma during use and includes plasma collector tubing 92, separator 205, plasma collector tubing 93 and one or more plasma collection bags, containers or reservoirs 94. A slide clamp 96 may be provided on plasma collector tubing 93. The plasma collection tubing assembly 90 may also be employed for further separation of the plasma component as will be described in more detail below.

The second spur 164b of the second integral plasma passageway 160b is interconnected to a plasma return tubing loop 166 to return plasma to donor/patient 4. For such purpose, the plasma return tubing loop 166 is interconnected to the top of the blood return reservoir 150 of the cassette assembly 110.

The plasma return assembly also returns plasma after separation or concentration. The post separation return includes tubing 963 which connects to tubing 962, spurs 140a and 140b as well as pumps engaging plasma tubing loop 142. Spur 144b is connected to plasma return loop or tubing 146 to deliver plasma to cassette reservoir 150 for ultimate delivery to the donor/patient 4. Similarly this sub-assembly can be used to provide replacement fluid through 962, 140a, tubing loop 142, 140b and 146 to return reservoir 150. If no replacement fluid is required the portion of tubing 962 related to the replacement fluid sub-assembly above the connection with tubing 963 may be omitted.

Although the plasma return assembly is shown returning plasma through tubing loop 142, the plasma could also be returned through another pump loop arrangement such as 162.

Figure 4:
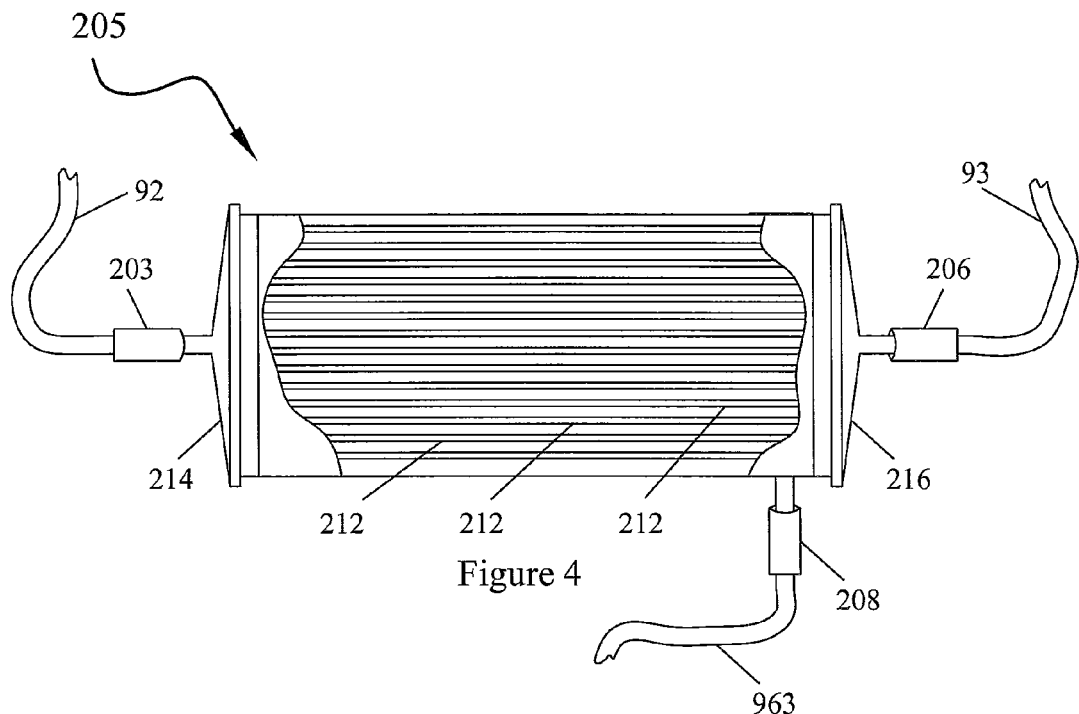
FIG. 4 is a schematic view of the plasma separation unit of FIGS. 1-3.

The plasma collection tubing assembly further includes a plasma separation sub-assembly shown in FIG. 4 including hollow fiber membrane separator or concentrator 205. Tubing 92 is interconnected to the inlet 203 of the separator 205. Tubing 93 is interconnected to the outlet 206 of the membrane separator 205. Plasma collection tubing assembly 90 also includes tubing 963, interconnected to second outlet 208 for returning plasma or proteins that are not to be collected. The plasma return assembly including return tubing 963 connects to tubing 962 and spur 140a as described above.

The plasma protein concentrator or plasma separator 205 includes inlet 203 in first end cap 214 and outlet 206 in the opposite end cap 216.

Hollow fiber membranes are arranged between the two end caps 214 and 216. Such hollow fiber membranes 212 include inter-capillary space (IC) within the fiber and an extra-capillary space (EC) outside the hollow fibers. The pore size of the membrane forming the hollow fibers may be selected so that components such as plasma or optionally, protein of selected molecular weight may pass between the IC and EC spaces. Thus, if separated plasma enters through tubing 92 and inlet 203 into the IC space, plasma and any proteins able to pass through the membrane pores to the EC space will pass through outlet 208 and tubing 963.

Table 1 below shows various protein factions and their molecular weight in kilodalton. The pore size of the membrane can be chosen to have a cut off value to pass through the membrane all but the desired protein fractions such as those given in the table. For example, the pore size could be such to pass all below 50 kilodaltons or the pore size could be selected to pass through the membrane those in a range in which the cut off value is selected between 50 kDa and 1300 kDa.

TABLE 1

| Constituent | Molecular Weight (kDa) |
|---|---|
| Cholesterol | 1,300 |
| IgM | 950 |
| Fibrinogen | 340 |
| Factor VIII | 100-340 |
| IgE | 190 |
| IgD | 175 |
| IgA | 160 |
| IgG | 150 |
| Haptogloblin | 100 |
| Albumin | 66 |
| A1Antitrysin | 54 |
| Factor VII | 50 |

For example, a membrane having a pore size such that only constituents with a molecular weight of less than 50 kDa will pass, all proteins in Table 1 will be collected through outlet 206 with only plasma less proteins being returned through outlet 208.

For another example, a membrane having a pore size such that only constituents having a molecular weight of less than 150 kDa will be returned, only a portion of the proteins with a molecular weight greater than 150 kDa will be collected. Plasma and other plasma proteins of less than 150 kDa molecular weight will pass through the membrane to outlet 208.

The RBC outlet tubing 64 of the blood inlet/blood component tubing assembly 60 is interconnected with integral RBC passageway 170 of cassette assembly 110 (FIG. 3). The integral RBC passageway 170 includes first and second spurs 170a and 170b, respectively. The first spur 170a is interconnected with RBC return tubing loop 172 to return separated RBC to a donor/patient 4. For such purpose, the RBC return tubing loop 172 is interconnected to the top of blood return reservoir 150 of the cassette assembly 110. The second spur 170b may be closed off if red blood cells are not to be collected or may be connected with an RBC collection tubing assembly 950.

RBC collection tubing assembly 950 includes RBC collector tubing 952, at least one RBC collection reservoir, container, or bag 954, and sterile barrier filter/drip spike assembly 956. One or a larger practical number (not shown) of RBC bag(s) 954 may be connected to the collector tubing 952. Moreover, although not shown here one or more white blood cell (WBC) filtration devices and/or RBC storage solution connections and/or bags may also be pre-connected to and/or be included as component parts of the RBC collection tubing assembly 950.

Vent bag tubing assembly 100 is also interconnected to the top of blood return reservoir 150 of cassette assembly 110. The vent bag tubing assembly 100 includes vent tubing 102 and a vent bag 104. During use, sterile air present since packaging within cassette assembly 110, and particularly within blood return reservoir 150, cyclically passes into and back out of vent tubing 102 and vent bag 104, as will be further described.

As illustrated in FIG. 3, pump-engaging tubing loops 122, 132, 142, 162 and 192 extend from cassette member 115 to yield an asymmetric arrangement thereby facilitating proper mounting of cassette assembly 110 on blood component separation device 6 for use.

In normal operation, whole blood will pass through needle assembly 30, blood removal tubing 22, cassette assembly 110 and blood inlet tubing 62 to processing vessel 352. The whole blood will then be separated into blood components in vessel 352. During product collection, RBCs and plasma will be passed out of vessel 352 through corresponding ports 520 and 456 for collection and subsequent plasma protein separation and/or return.

In the cassette assembly the reservoir 150 having upper and lower ultrasonic sensors (not shown) is provided such that, during the blood processing mode, return blood will be removed from reservoir 150 during each blood return/replacement delivery sub-mode and accumulated during each blood removal sub-mode. When uncollected platelets and plasma (and potentially white blood cells) or red blood cells not collected and/or replacement fluid(s) have accumulated in reservoir 150 up to upper ultrasonic level sensor (not shown), operation of the pump 1090 associated with pump loop 192 will be initiated to remove the blood or replacement components from reservoir 150 through 190a, 192, and 190b and transfer the same back to the donor/patient 4 via the return/delivery tubing 24 and needle assembly 20. When the fluid level in the reservoir 150 drops down to the level of the lower ultrasonic level sensor, the return/delivery peristaltic pump 1090 will automatically turn off reinitiating blood removal sub-mode. The cycle between blood removal and blood return/replacement delivery sub-modes will then continue until a predetermined amount of platelets, RBCs or other collected blood components have been harvested.

Pump 1040 is associated with tubing pump loop 142, pump 1066 is associated with tubing loop 162, pump 1030 is associated with tubing loop 132, pump 1020 is associated with tubing loop 122, and pump 1090 is associated with tubing loop 192 when the cassette 110 is mounted on pump/valve/sensor assembly 1000.

The channel assembly 200 includes a channel housing 204 which is disposed on the rotatable centrifuge rotor assembly 568 (FIG. 1) and which receives a disposable blood processing vessel 352.

The channel housing 204 provides a mounting for the blood processing vessel 352 such that the blood may be separated into the blood component types in a desired manner. In this regard, the channel housing 204 includes a generally concave channel (not shown) in which the blood processing vessel 352 is positioned.

The blood processing channel vessel 352 is disposed within the channel 204 housing such that blood can be provided to the blood processing vessel 352 during rotation of the channel housing 204, to be separated into its various blood component types by centrifugation, and to have various blood component types removed from the blood processing vessel 352 during rotation of the channel housing 204. Moreover, the channel also desirably interacts with the blood processing vessel 352 during centrifugation (e.g., by retaining the blood processing vessel 352 in the channel and by maintaining a desired contour of the blood processing vessel 352). In addition, the channel allows for a blood priming of the blood processing vessel 352 (i.e., using blood as the first liquid which is provided to the blood processing vessel 352 in an apheresis procedure).

The blood processing vessel 352 is disposed within the channel of the channel housing 204 for directly interfacing with and receiving a flow of blood in an apheresis procedure. The use of the blood processing vessel 352 alleviates the need for sterilization of the channel housing 204 after each apheresis procedure and the vessel 352 may be discarded to provide a disposable system. The blood processing vessel 352 is constructed such that it is sufficiently rigid to be free-standing in the channel. Moreover, the blood processing vessel 352 is also sufficiently rigid so as to be loaded in the channel having the above-identified configuration. However, the blood processing vessel 352 must also be sufficiently flexible so as to substantially conform to the shape of the channel during an apheresis procedure. Further details of the blood processing vessel and parts of the apheresis system are described in U.S. Pat. No. 6,514,189B1.

As shown in FIG. 2, blood is introduced into the interior of the blood processing vessel 352 through a blood inlet port 392 from inlet tubing 62. The blood inlet port 392 extends into an interior portion of the blood processing vessel 352.

Blood which is provided to the blood processing vessel 352 by the blood inlet port 392 is separated into at least RBCs, and/or plasma.

Separated plasma exits the blood processing vessel through port 456 and tubing 68. Separated red blood cells exit the blood through port 520 and tubing 64.

The apheresis system includes various valve assemblies shown schematically at 1120, 1110, and 1100 in FIG. 3. These valves are part of the pump/valve/sensor assembly 1000.

The apheresis system described herein provides for continuous separation of red blood cells (RBCS) and/or plasma with a continuous plasma separation step. For example, continuous separation may be provided with contemporaneous collection of both RBCs and plasma and/or with collection of either RBCs or plasma separately. For further plasma separation, plasma may be collected either with RBC's or alone. The non-collected components are re-infused back to the donor. Note, the buffy coat components, namely platelets and WBCs, are not collected separately as described. Rather, these components may remain with the RBCs throughout these procedures and may either be filtered out subsequently, e.g., the WBCs through a leukoreduction filter or the like; or may remain with the RBC product(s) or be returned to the donor. The plasma product(s) may remain platelet-poor and contain no WBCs (or at least within promulgated minimum safety ranges).

In the present embodiment only the option related to the collection of RBCs and plasma contemporaneously or plasma alone will be described though the collection of platelets may be an additional option. In one approach where both plasma and RBCs are to be collected, the blood apheresis system 2 may be employed to collect RBCs and plasma contemporaneously for a first time period, and then collect either plasma or red blood cells for a second period. This may include double red blood cell products or double plasma products, and the double product quantity may be configurable by the user.

Replacement fluid(s) are also optionally administrable within the procedures of the present invention. Sterile saline solution(s) is one of the optional replacement fluids considered for use herein. Thus, if/when large fluid amounts of plasma and/or RBCs are taken from a donor/patient, replacement fluid(s) may be delivered in return to leave the donor/patient adequately hydrated.

The initiation of blood processing provides for the collection of plasma in one or more reservoir(s) 94 and/or the collection of red blood cells in one or more reservoir(s) 954. Alternatively, either RBC collection in reservoir(s) 954 or plasma collection in reservoir(s) 94 may also be selectively completed in separate procedures. During either collection procedure, blood component separation device 6 preferably controls the initiation and termination of successive blood removal and blood return. Additionally, blood component separation device 6 will control the plasma and RBC collection processes according to predetermined protocols, preferably including control over the valve assemblies 1100, 1110 and 1120 of the pump/valve/sensor assembly 1000, and/or the appropriate pumps 1020, 1030, 1040, 1066 and/or 1090.

Initially, blood priming is carried out to prime the disposable system 10. During blood priming, it may be desirable that the component separation begins even during the priming stage, and that some plasma is collected. Thus plasma may flow out through the outlet port 456 to tubing 68.

Following and/or contemporaneously with the blood priming phase, blood separation control device 6 provides control signals to pump/valve/sensor assembly 1000 so that the optional replacement fluid lines may also be primed. In particular, replacement fluid valve assembly 1100 is opened and replacement fluid inlet pump 1040 is switched on to provide for the pumping of saline solution (or other replacement fluid(s)) through replacement fluid inlet tubing 962 and the replacement fluid tubing loop 142a into replacement fluid introduction tubing line 146 for initial collection in cassette reservoir 150, though this initial priming collection will likely and preferably does constitute a small amount of replacement fluid(s).

After priming is completed, yet still during the set-up phase, blood component separation device 6 may provide appropriate control signals to the pump/valve/sensor assembly 1000 such that all separated blood components flowing out of processing vessel 352 will first pass to return/delivery reservoir 150. Optionally, one or more cycles of separation and return of all blood components back to the donor may be performed before collection. Also, blood component separation device 6 may continue operation of blood inlet pump assembly 1030 associated with pump loop 132 during one or more these initial blood component return sub-modes.

To establish the desired AC ratio, blood component separation device 6 provides appropriate control signals to anticoagulant peristaltic pump 1020 so as to introduce anticoagulant into the blood inlet flow at a predetermined rate. The inlet flow rate of anti-coagulated blood to blood processing vessel 352 may be limited by a predetermined, maximum acceptable anticoagulant infusion rate (ACIR) to the donor/patient 4.

When collection begins, blood component separation device 6 may provide control signals so that plasma divert valve assembly 1110 switches to divert the flow of separated plasma pumped from vessel 352 through plasma outlet tubing 68 and plasma tubing loop 162 into plasma collector tubing 92 through inlet 203 of membrane separator 205. See also FIG. 5 which shows a simplified view of the apheresis system. Additionally, if plasma is to be collected alone, red blood cells will continue to flow from vessel 352 through outlet tubing 64 through return tubing loop 172 and into blood return reservoir 150. However, if RBCs are to be collected, contemporaneously with plasma, then red blood cell valve 1120 switches to divert the flow of separated RBCs flowing from tubing 64 to and through spur 170b (of cassette 110) and into and through tubing line 952 to the one or more RBC collection reservoir(s) 954.

During any of the collection processes, one or more replacement fluid(s) may also be delivered to the donor/patient 4. Thus, whenever the separation device 6 is in a collection rather than the return mode, the replacement fluid inlet valve assembly 1100 may also be opened and the replacement fluid pump 1040 starts to flow replacement fluids from the fluid source (not shown) through tubing line 962, cassette passageways 140a and 140b, and tubing loops 142 and 146 into the reservoir 150.

During separation and collection, channel housing 204 can be typically driven at a rotational velocity of about 3000 rpms to achieve the desired hematocrit during the both the setup and component collection phases. Correspondingly, the blood inlet flow rate to vessel 352 may be established at below about 64.7 ml/min. The desired hematocrit can be reliably stabilized by passing about two whole blood volumes of vessel 352 through vessel 352 before the RBC and/or plasma collection phases are initiated.

To initiate an RBC collection phase, blood component separation device 6 provides an appropriate control signal to RBC divert valve assembly 1120 so as to direct the flow of RBCs removed from blood processing vessel 352 into RBC collection reservoir 954. Upon and/or simultaneously with initiation of RBC collection, replacement fluid valve assembly 1100 is switched to optionally provide replacement fluid flow also into the reservoir 150.

Separated RBCs are not pumped post-separation out of vessel 352 through line 64 for collection, but instead are moved out of vessel 352 and through extracorporeal tubing circuit 10 by the relative pressure of the blood inlet flow to vessel 352 (as this may be modified by the plasma outlet pressure through the plasma outlet port 456). Consequently, trauma to the separated and collected RBCs is minimized.

With respect to plasma collection, which may occur separate from or continuously with red blood cell collection, the separated plasma is pumped via pump 1066 through the plasma collect line 92 through filter separator or concentrator 205 to plasma component collection bag 94 through line 93.

The separated plasma is pumped out of rotor 352 through port 456, line 68, passageway 160*a*, tubing 162, passageway 160*b*, by pump 1066 around which tubing 162 extends and flows via plasma collect line 92 into filter or separator 205. The fraction of plasma proteins that do not pass through the filter membrane from the IC to the EC side flow into storage bag 94. The remainder of the plasma and/or proteins that pass to the EC side flow out of the filter 205 through outlet 208, tubing 963, 962, passageway 140*a*, tubing loop 142, passageway 140*b*, tubing 146, to reservoir 150 and back to the donor 4. An enriched plasma product, which may contain several times the normal amount or an increased concentration of the desired protein, could be produced by simply processing more plasma through the filter, concentrator or separator 205.

Following collection of the desired quantity of red blood cells, the separation and collection of plasma proteins, and after blood separation device 6 has provided control signals to divert assemblies 1110 and 1120 so as to divert the respective separated plasma and separated RBC flows to reservoir 150, if further blood processing is not desired, rinse back procedures may then be completed. The plasma pump 1066 is set at the full plasma rate equal to rate of the return/delivery pump 1090 for rinse back.

At the end of the procedures, the plasma bag(s) 94 and the red blood cell reservoir(s), if any, 954 may be disconnected from the extracorporeal tubing circuit 1.

The pore size of the filter 205 determines whether all proteins are collected in container 94 or only those proteins of sufficiently high molecular weight.

Figures 5, 7:
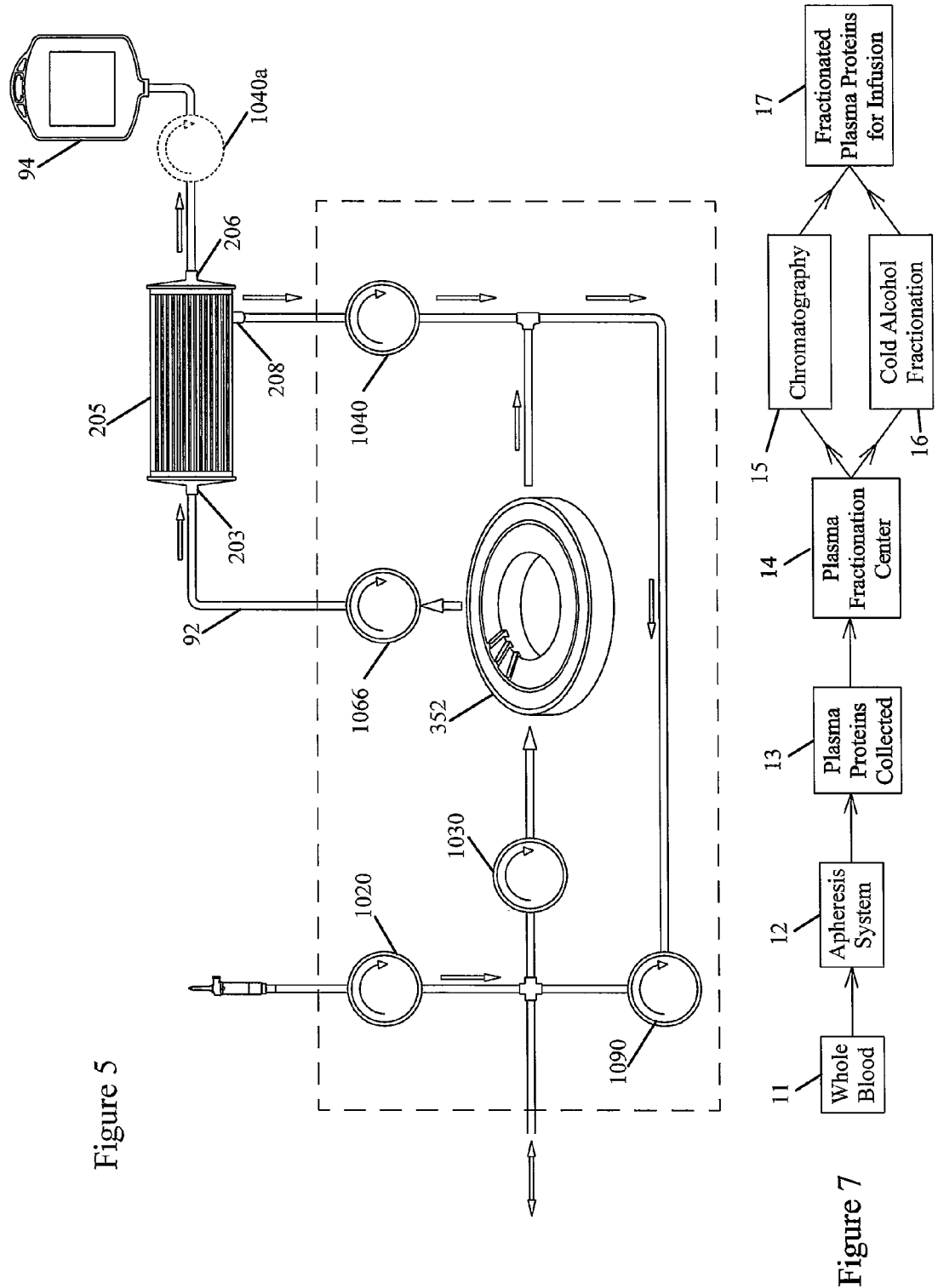
FIG. 5 is a schematic view with details removed of the system of FIG. 1.
FIG. 7 is a block diagram illustrating a process using collected apheresis plasma proteins for further fractionation.

The simplified FIG. 5 also indicates another option. As shown in FIG. 5 the plasma entering the plasma separator 205 is pumped on the inlet side 203 by pump 1066 and also the outlet (EC) side 208 by pump 1040. However the locations of the pumps can be varied. For example, as shown in FIG. 5 there also may be a pump on the IC exit side, (illustrated in phantom lines as 1040*a*). This pump may be used with the inlet pump 1066 alone, (no pumping through 1040 on the EC side) or it may be used with pump 1040 alone, (no pumping through 1066 into the inlet or IC side. Thus two pumps are utilized but the exact locations of such pumps may be varied.

Having pump 1040*a* pump on the IC side from 206 provides flow through the membrane by positive pressure on the IC side thus avoiding any degassing of the fluid as may occur using pumps 1066 and 1040 which exerts negative pressure on the EC side. If the membrane 212 becomes blocked when pump 1040*a* is used the compression force of the rollers of pump 1040*a* could be such that they will lift sufficiently and provide less occlusion for the over volume or pressure. Thus it can function as a pressure relief valve.

This continuous apheresis procedure permits desirable proteins to be collected and removed from a donor with the remainder of the plasma proteins being returned to the donor. This enables maximum collection and concentration of the desired proteins, instead of the smaller amount of desired protein contained within a single donation.

Using this procedure, plasma protein fractions may be collected at the same time as other cellular components. Specifically, desired plasma proteins may be collected from a donor, while the undesired components may be returned to the donor. This would enable greater amounts of desired plasma proteins to be collected from a single donor, without increasing the risk to the donor as the amount of fluid volume removed from a donor would not be detrimental. More plasma can be processed resulting in the collection of increased amounts of plasma protein. However, from the donor perspective the increased collection of proteins can be collected with the same volume removal as a typical plasma collection.

The final concentration of the protein-enriched product could be adjusted by adjusting the ratio of the plasma flow into the filter and the plasma flow out of the filter. This can be done by adjusting pump speed of pump 1066, 1040 or 1040*a*. For example, if the membrane excluded all proteins and the flow rate through the filter was half that of the plasma flow into the filter, the resultant concentration of the proteins would be double that of normal donor plasma.

If it is desired to collect high molecular weight proteins, the filter/column 205 could separate on a continuous basis the albumin and other low molecular weight proteins and return them to the donor, while collecting higher molecular weight fractions such as fibrinogen, IgG, von Willebrand factor and factor VIII.

Figure 6:
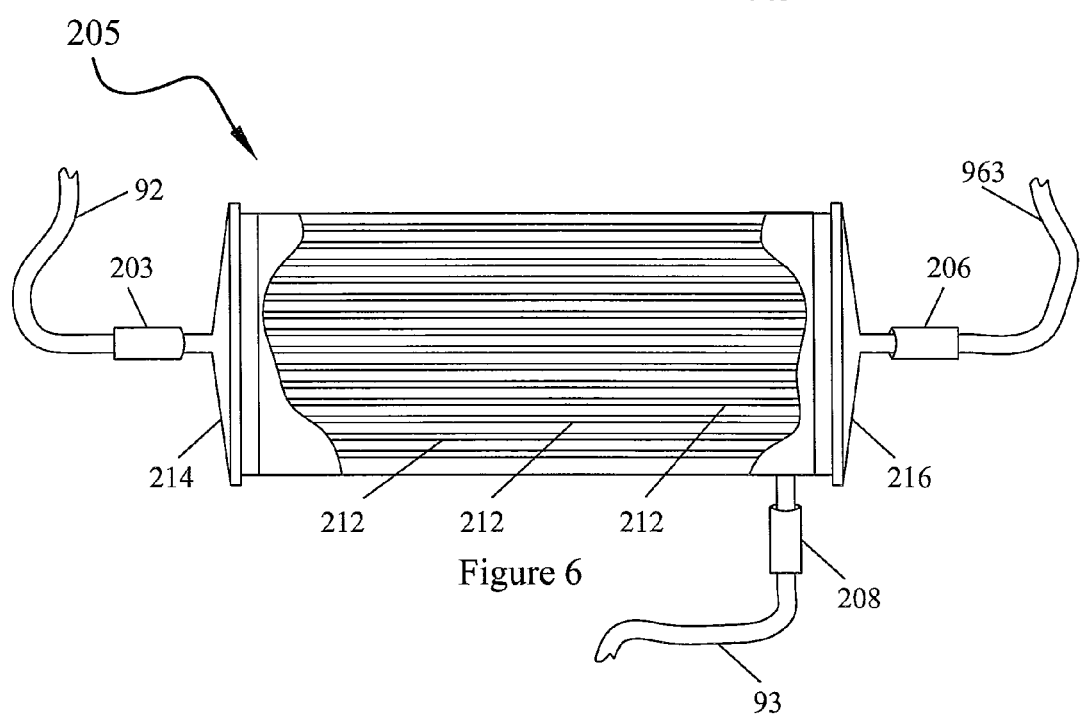
FIG. 6 is a schematic view of an alternative connection for the plasma separation unit for collection of low molecular weight fractions.

An alternative arrangement for the filter concentrator could also be provided as shown in FIG. 6. If lower molecular weight proteins are desired, the higher molecular weight proteins could be returned to the donor, while the lower molecular weight proteins are collected by changing the tubing so that those that pass through the membrane are collected rather than returned. In this configuration outlet 208 would be connected to tubing 93 with outlet 206 being connected to tubing 963 for return to the donor.

Also, although the above is described with respect to the separated plasma entering the IC side of the membrane, such plasma could enter the EC side with the low molecular constituents passing to the IC side through the membrane. Collection would be through port 206 if low molecular fractions are desired or through port 208 if higher molecular weight fractions are collected.

As described above, such separation specificity can be accomplished by selecting membranes which have pore sizes which correspond to the molecular weight of the desired protein.

The high concentration protein collected could be used to enrich the plasma of a patient for therapeutic purposes. The high-concentration product may also be used for additional fractionation as described below where its yield of proteins would be much higher compared to normal plasma and thus produce an increased amount of protein concentrate products.

FIG. 7 illustrates, in block diagram form, the process of taking whole blood from a donor 11 (whole blood) and using apheresis apparatus 12 as described above to collect a concentrated protein fraction. The plasma proteins 13 from the apheresis process may optionally be provided to plasma fractionation center 14, and optionally pooled with other collections, for further fractionation or concentration of such product utilizing a known plasma fractionation process such as cold alcohol fractionation 16 (also known as Cohn fractionation) or chromatography 15. Other known fractionation processes could be used. This process could be used to provide a highly concentrated plasma protein infusion product 17 such as IVIG or clotting factor. Cold alcohol fractionation includes the addition of alcohol to the collected apheresis protein product while simultaneously cooling the protein product. This causes the selected plasma proteins to precipitate out of any remaining plasma or other non-selected proteins. Chromatography includes the method of passing the apheresis plasma proteins through a stationary phase to separate out further the desired proteins from other proteins and any remaining plasma. These processes result in a further concentrated product of the desired proteins. Such product may be frozen until needed as an infusion product. Example

TABLE 2

| Test Run: Sample ID | Plasma Assay Results | | |
|---|---|---|---|
| | PC6 Total Prot g/dl | Albumin g/dl | IgG mg/dl |
| Incoming Plasma1 | 5.8 | 3.2 | 970 |
| Incoming Plasma2 | 5.7 | 3.2 | 995 |
| Run 1 HMW1 | 11 | 6.4 | 2105 |
| LMW1 | <1 | <1 | <200 |
| Run 2 HMW2 | 10.7 | 6.4 | 2072 |
| LMW2 | <1 | <1 | <200 |
| LMW3 | <1 | <1 | <200 |

Table 2 shows an assay result for two runs on an apheresis system with a plasma concentrator or separator 205 similar to that described above with respect to FIG. 4. HMW or high molecular weight indicates the amount of total protein, albumin, or IgG immunoglobulin exiting the separator 205 at outlet 206. LMW, low molecular weight, indicates the total amount of protein, albumin or IgG assayed at outlet 208.

Table 3 illustrates protein predictions based on volume amounts for the apheresis system with the plasma separator shown in FIG. 4. For each run, the inlet pump 1030 flow rate (inlet) is given. Also listed is plasma flow rate as determined by plasma collect pump 1066 corresponding to the flow rate at 203. Also given is the flow rate in line 93 or the exit 206 called the HMW rate. The low molecular flow rate in conduit or line 963 as pumped by pump 1040 is denoted at LMW. The pressure across the membrane such as the membrane of hollow fibers 212 or the trans membrane pressure TMP is also given. The pump ratio is the ratio of the plasma collect flow rate over the HMW flow rate (where high molecular weight proteins are collected). The volume ratio is the amount entering inlet 203 over amount exiting 206 for a specific period of time. The volume is readily determined from the flow rate per unit time.

The measured concentration for total protein, albumin, IgG, and the average are given as determined from collect bag 94.

The concentration ratio and the volume ratio show close correspondence. As can be seen from the example the difference is 5% or less. From this data it can be seen that the protein concentration can be predicted from the volume ratio.

A method of predicting the protein concentration may include determining the volume passing the inlet 203 for a period of time and determining the volume at the outlet 206 for the same period of time. The inlet volume may be determined by the number of rotations of pump 1066 or flow rate. The outlet volume can be determined by volume measurement in bag 94 or by the number of rotations or flow rate of pump 1040. Taking the inlet volume over the outlet volume yields the volume ratio. This ratio may be used as the average concentration ratio for the proteins being collected in bag 94.

For example, using the principals set forth above:

Volume In−Volume Uncollected=Volume Out

Volume In/Volume Out=Volume In/Volume In−Volume Out=Volume Ratio

The volume ratio, once determined, is an approximation of the concentration ratio.

As described above, the volume ratio is related to flow rate per unit time. Selection of flow rate, including flow rate into the concentrator 205 as compared to flow rate through the outlets 206, 208 can be used to select a particular protein concentration for the final collected product.

It will be apparent to those skilled in the art that various modifications and variations to the methods and structure of the present invention without departing from its scope. Thus it should be understood that the invention is not be limited to the specific examples given. Rather, the invention is intended to cover modifications and variations provided they come within the scope of the following claims and their equivalents.

TABLE 3

| | Inlet (inst.) (ml/min) | Plasma (ml/min) | LMW (ml/min) | LMW (g) | HMW (ml/min) | HMW (g) | TMP (mmHg) | Pump Ratio Command rate | Volume Ratio Volume meas | Measured Conc Ratio Total Prot | Measured Conc Ratio Albumin | Measured Conc Ratio IgG | Measured Conc Ratio Avg | Conc Ratio/ Volume Ratio % |
|---|---|---|---|---|---|---|---|---|---|---|---|---|---|---|
| Run 1 | 50 | 20 | 13 | 53.6 | 7 | 51.1 | 190 | 2.86 | 2.10 | 1.91 | 2.00 | 2.14 | 2.02 | −4% |
| Run 2 | 50 | 20 | 13 | 46.4 | 7 | 44.6 | 212 | 2.86 | 2.09 | 1.86 | 2.00 | 2.11 | 1.99 | −5% |

The invention claimed is:

1. A method of collecting plasma fractions from whole blood comprising:
   rotating a separation vessel;
   separating plasma from other blood components of the whole blood in the rotating separation vessel;
   providing separated plasma from the rotating separation vessel to a plasma separator;
   separating the plasma into at least one fraction including plasma proteins using the plasma separator;
   collecting the at least one fraction; and
   determining the ratio of the volume of separated plasma provided to the plasma separator in the providing step to the volume of the at least one fraction in the collecting step to determine a volume ratio;
   predicting the concentration ratio of the plasma proteins in the at least one fraction from the volume ratio.

2. The method of claim 1 further comprising:
   returning any plasma and plasma proteins not collected in the collecting step back to the donor.

3. The method of claim 2 wherein the returning step comprises pumping any plasma and plasma proteins not collected back to the donor.

4. The method of claim 2 further comprising;
   separating red blood cells from other blood components in the rotating separation vessel;
   collecting the separated red blood cells.

5. The method of claim 1 further comprising;
separating red blood cells from other blood components in the rotating separation vessel;
collecting the separated red blood cells.

6. The method of claim 1 wherein the determining the ratio step comprises:
determining the volume of separated plasma entering the plasma separator for a specified time period;
determining the volume exiting the plasma separator for the specified time period for collection in the collecting step.

7. The method of claim 1 further comprising:
providing the plasma separator comprising a hollow fiber membrane selected so that the separating the plasma step comprises:
passing plasma and any plasma proteins not to be collected through the membrane.

8. The method of claim 7 wherein the passing step comprises passing plasma and any low molecular weight plasma proteins through the membrane.

9. The method of claim 1 further comprising pumping plasma into the plasma separator.

10. The method of claim 1 further comprising:
providing the plasma separator comprising a hollow fiber membrane selected so that the separating step comprises passing plasma and any plasma proteins to be collected through the membrane.

11. The method of claim 1 further comprising fractionating the at least one collected fraction in a plasma fractionation process to further concentrate the desired proteins in the at least one fraction.

12. The method of claim 11 wherein the step of fractionating the at least one collected fraction comprises precipitating out the desired proteins using cold alcohol fractionation.

13. The method of claim 11 wherein the step of fractionating the at least one collected fraction comprises passing the collected fraction through a stationary phase to concentrate the desired plasma proteins.

14. A method of collecting plasma fractions from whole blood comprising:
rotating a separation vessel;
separating plasma from other blood components of the whole blood in the rotating separation vessel;
providing separated plasma from the rotating separation vessel to a plasma separator;
separating the plasma into at least one fraction including plasma proteins using the plasma separator;
providing the plasma separator comprising hollow fiber membranes selected so that the separating the plasma step comprises:
passing plasma and any plasma proteins not to be collected through the hollow fibers of the membrane;
collecting the at least one fraction; and
returning any plasma and plasma proteins not collected in the collecting step back to the donor;
determining the ratio of the volume of separated plasma provided to the plasma separator in the providing step to the volume of the at least one fraction in the collecting step to determine a volume ratio;
predicting the concentration ratio of the plasma proteins in the at least one fraction from the volume ratio.

15. The method of claim 14 further comprising:
separating red blood cells from other blood components in the rotating separation vessel;
collecting the separated red blood cells.

16. The method of claim 14 further comprising pumping plasma into the plasma separator.

17. The method of claim 14 wherein the passing step comprises passing plasma and any low molecular weight plasma proteins through the membrane.

18. An apheresis plasma separation system comprising:
a blood component separation device;
a rotor;
a separation vessel mounted on the rotor for rotating therewith wherein blood is separated into plasma and other components in the separation vessel during rotation of the rotor;
a plasma separator fluidly connected to the separation vessel to receive the separated plasma from the rotating separation vessel;
a membrane comprising a hollow fiber membrane in the plasma separator wherein the membrane can separate at least some plasma proteins from the separated plasma;
a collection container fluidly connected to the plasma separator for collecting the separated plasma proteins from the plasma separator;
an inlet on the plasma separator;
an outlet on the plasma separator;
wherein the blood component separation device is configured to control the flow of plasma such that the volume of separated plasma through the inlet as compared to the volume of collected plasma proteins through the outlet for a period of time corresponds to the concentration of the plasma proteins in the collection container.

19. The system of claim 18 wherein the other components include at least a red blood cell component and further comprising:
at least one red blood cell collection container wherein any separated red blood components are collected in the red blood cell collection container.

20. The system of claim 19 wherein the pump acts as a pressure relief value in instances of over pressure.

21. The system of claim 18 further comprising a return assembly fluidly connected to the plasma separator to return any uncollected plasma or plasma proteins back to a donor.

22. The system of claim 21 further comprising a pump in the return assembly for pumping any uncollected plasma or plasma proteins back to the donor.

23. The system of claim 21 wherein the membrane has a pore size such that uncollected plasma and low molecular weight proteins pass through the membrane and from the plasma separator to the return assembly.

24. The system of claim 23 wherein the membrane has a pore size such that the cut off for uncollected plasma and any plasma proteins for passage through the membrane is in the range from 50 to 1300 kDa.

25. The system of claim 23 wherein the membrane has a pore size such that cut off for uncollected plasma and any plasma proteins for passage through the membrane is less than 150 kDa.

26. The system of claim 23 wherein the membrane has a pore size such that the cut off for uncollected plasma and any plasma proteins for passage through the membrane is less than 50 kDa.

27. The system of claim 18 further comprising a pump for pumping separated plasma from the separation vessel to the plasma separator.

28. The system of claim 18 further comprising a pump for pumping separated plasma proteins from the plasma separator to the collection container.

29. A method of predicting the concentration of proteins to be collected using a plasma separator comprising:
determining the inlet volume of fluid entering a plasma separator for a period of time;

determining the exit volume of plasma proteins separated from plasma in the plasma separator and exiting the plasma separator for such period of time;

predicting the concentration of plasma proteins exiting the plasma separator by determining the ratio of the inlet volume over the exit volume.

30. The method of claim 29 comprising:

determining the volume entering a plasma separator comprises;

determining the flow rate of plasma into the plasma separator.

31. The method of claim 29 wherein determining the exit volume comprises:

determining the volume of the plasma and any plasma proteins separated from the plasma proteins to be collected comprising:

determining the flow rate of the remaining plasma and plasma proteins exiting from the plasma separator; and using the volume of the remaining plasma and plasma proteins to predict the concentration of the separated plasma proteins.

32. The method of claim 29 further comprising selecting a desired protein concentration to be collected comprising varying the ratio of the inlet volume and the outlet volume to achieve the selected concentration.

33. The method of claim 32 wherein the ratio of the inlet volume to the outlet volume is varied by changing the flow rate to the inlet as compared to the flow rate at the outlet.

* * * * *